United States Patent [19]

Beck

[11] Patent Number: 4,919,929
[45] Date of Patent: Apr. 24, 1990

[54] MAMMAL IMMUNIZATION

[75] Inventor: Lee R. Beck, Birmingham, Ala.

[73] Assignee: Stolle Research & Development Corporation, Birmingham, Ala.

[21] Appl. No.: 910,297

[22] Filed: Sep. 17, 1986

Related U.S. Application Data

[63] Continuation of Ser. No. 576,001, Feb. 1, 1984, abandoned.

[51] Int. Cl.⁵ .............................................. A61K 39/00
[52] U.S. Cl. ..................................... 424/88; 424/89; 424/90; 424/91; 424/92; 424/85.1; 424/85.2; 424/85.8; 424/86; 424/87; 424/438; 424/462; 424/489; 424/497; 424/443; 424/459; 424/484; 424/486; 424/490; 424/457; 424/458; 604/890.1; 128/1 R
[58] Field of Search ............... 604/890, 894; 128/1 R; 424/88–92, 85.1, 85.2, 85.8, 438, 443, 457–459, 462, 484, 486, 489, 490, 497

[56] References Cited

U.S. PATENT DOCUMENTS

| | | | |
|---|---|---|---|
| 3,911,108 | 10/1975 | Singh | 424/86 |
| 4,150,116 | 3/1979 | Taubman et al. | 424/88 |
| 4,166,800 | 9/1979 | Fony | 424/32 |
| 4,329,332 | 5/1982 | Couvreur et al. | 424/88 |
| 4,332,790 | 6/1982 | Sozzi et al. | 424/92 |
| 4,338,298 | 7/1982 | Myers | 424/88 |
| 4,377,569 | 3/1983 | Phymate | 424/85.8 |
| 4,432,964 | 2/1984 | Shell et al. | 424/22 |
| 4,439,199 | 3/1984 | Amkrauts et al. | 604/894 |
| 4,450,150 | 5/1984 | Sidman | 128/1.1 |
| 4,484,923 | 11/1984 | Amkrauts et al. | 604/894 |
| 4,489,055 | 12/1984 | Couvreur et al. | 424/92 |
| 4,525,340 | 6/1985 | Lange et al. | 604/890 |
| 4,686,098 | 8/1987 | Kopchick et al. | 435/177 |

OTHER PUBLICATIONS

DeGeeter et al, CA vol. 99, 1983, #157232u.
*American Scientific*, 1979, pp. 66–73, Blackshear.

*Primary Examiner*—Garnette D. Draper
*Attorney, Agent, or Firm*—Oblon, Spivak, McClelland, Maier & Neustadt

[57] ABSTRACT

Mammals are brought to a specific state of immunization by administering an amount of an antigenic substance sufficient to elicit an immunization response to said mammal, said antigenic substance being incorporated within a shaped structure of a biocompatible matrix material.

14 Claims, 1 Drawing Sheet

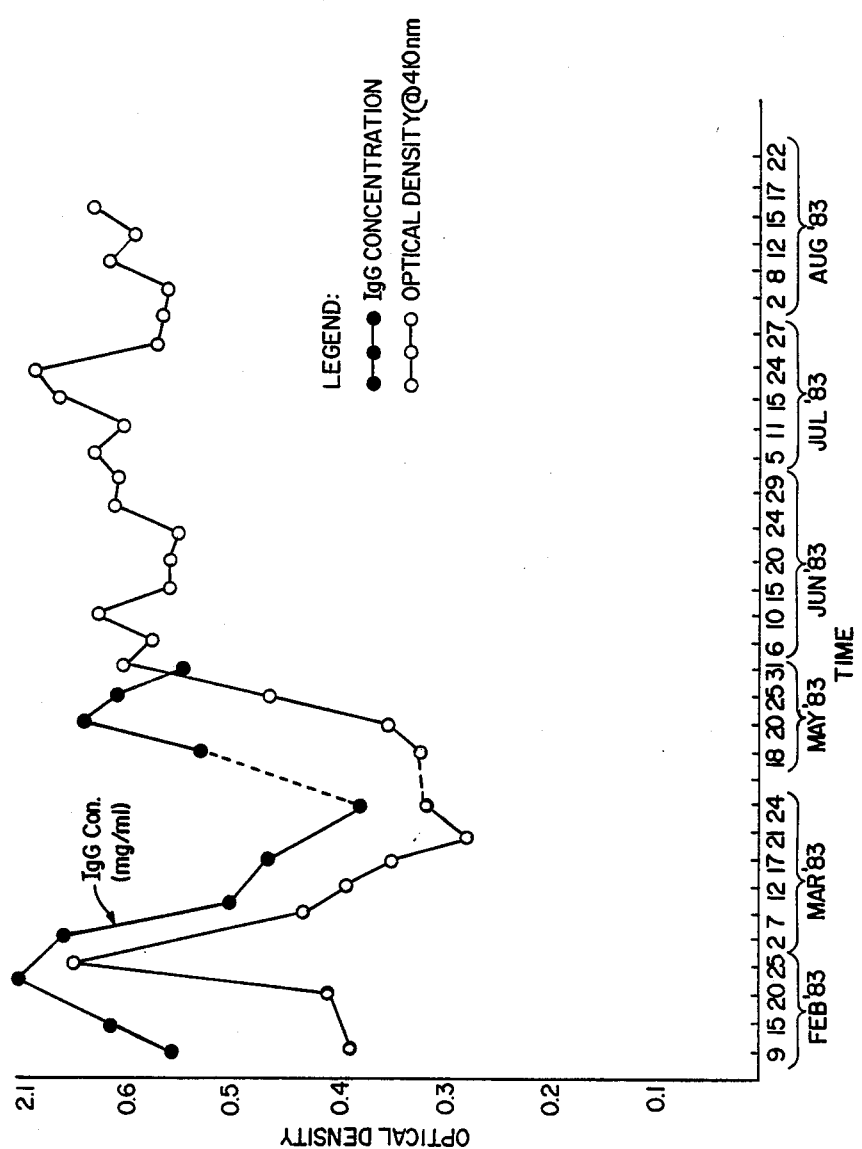

MAMMAL IMMUNIZATION

This application is a continuation of application Ser. No. 576,001, filed Feb. 1, 1984, now abandoned.

BACKGROUND OF THE INVENTION

1. Field of the Invention:

The present invention relates to a method of immunizing mammals by inoculation with antigenic substances. More particularly, the invention relates to an improved method of inoculating bovid animals in such a way as to achieve higher antibody titer and lymphokinen levels than can be achieved by conventional inoculation procedures.

2. Description of the Prior Art:

Through recent studies, it has been found that the milk taken from a bovid animal such as a cow which has been treated with a spectrum of bacterial antigens is useful in alleviating or eliminating some pathogenic conditions when ingested by a host subject. By virtue of the high antibody titer or the lymphokinen levels of the milk, a subject who ingests the milk or product derived from the milk increases the antibody or lymphokinen count of his own system thereby being able to more effectively resist and defeat a given pathological condition(s) against which the given immune regulatory factors are effective.

For example, U.S. Pat. 4,284,623 discloses a method of treating inflammation in a host subject by way of the host subject, exhibiting an inflammatory condition, ingesting milk or a product derived therefrom which has been obtained from a bovid such as a cow which has been inoculated with a spectrum of antigens. The antigens can be any combination of bacterial, viral or cellular antigens with the only substantive restrictive factor being that the bovid being inoculated must be able to respond to the antigen challenge by exhibiting a state of immune sensitivity. This state of immune sensitivity is reflected by a high antiinflammatory factor or antibody factor in the milk obtained from the animal. The antiinflammatory factor or immune regulatory factor is a product of the sensitized lymphocyte, more generally referred to as a lymphokinen. The milk obtained in this fashion is capable of alleviating inflammation in a subject who ingests the milk or product derived from said milk.

U.S. Pat. 4,324,782 describe another example of the therapeutic effectiveness of an antibody containing bovid milk. Cows, immunized with one or more strains of *Streptococcus mutans* antigen, produce an antibody-containing milk, which, when ingested by a host subject, provides the host subject with antibodies effective against the growth of *S. mutans* bacteria in the oral cavity thereby aiding in the prevention of tooth decay.

Other prior art procedures are known for producing milk which have a variety of therapeutic effects. Heinbach, U.S. Pat. No. 3,128,230 has described milk containing globulins of $\alpha$, $\beta$, $\gamma$ components, by inoculating a cow with antigenic mixtures. Petersen (U.S. Pat. No. 3,376,198 and Canadian Pat. No. 587,849), Holm, U.S. patent application (published) Ser. No. 628,987, now abandoned and Tunnak et al, British Pat. No. 1,211,876 have also described antibody-containing milks.

All of the above known procedures for obtaining antibody-containing milk are disclosed as being obtained by standard immunization procedures well-known to skilled veterinarians. Usually, a bovid animal is immunized by an initial injection of antigen-containing fluid with the initial injection being followed at specific tim intervals by booster injections in order to raise the antibody titer of the bovid to an immune state. If, after a first series of booster injections, the animal is not in a sufficiently immune state, the animal must be inoculated with a second series of injections in order to reach the desired level of immunity.

In view of the problems associated with inoculating a subject bovid animal to obtain an antibody titer level in the animal which is sufficient for the purposes desired with respect to frequency of inoculation and the titer levels which can be achieved, a need continues to exist for a method by which high antibody and/or lymphokinen levels in a bovid animal can be achieved with minimal injections of antigenic material to reach the desired titer levels.

SUMMARY OF THE INVENTION

Accordingly, one object of the present invention is to provide a method of achieving an immune state in a mammal, particularly a bovid animal, with fewer inoculations of a given antigenic substance(s) than required by conventional immunization procedures.

Another object of the present invention is to provide a method of producing antibodies and lymphokinen factors in milk.

Briefly, this object and other objects of the present invention as hereinafter will become more readily apparent can be attained in a method of placing a mammal in an immunized state by administering an amount of an antigenic substance sufficient to elicit an immunization response, the antigenic substance being administered in the form of a shaped structure of a biocompatible matrix material. In an alternative embodiment of the method the immunized state is attained more rapidly by simultaneously administering antigenic substance containing shaped matrix material to the mammal and inoculating the mammal with liquid antigenic substance.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing, wherein:

the FIGURE is a graph in which optical density and IgG titer level are plotted as a function of time for cattle which have been immunized against the S-100 spectrum of bacterial antigens.

DETAILED DESCRIPTION OF THE PREFERRED EMBODIMENTS

The heart of the present invention is the discovery that when a mammal is implanted with a biocompatible matrix material shaped into an object containing at least one antigenic substance, an immunization response can be attained with as few as only one treatment of antigen-containing shaped matrix material. An additional and unexpected aspect of the discovery is that by the use of the antigen-containing shaped matrix material, antibody titer and lymphokinen levels greater than normally reached by conventional methods of inoculation or injection can be achieved.

Any mammal ca be treated with an antigenic substance by the technique of the present invention. A preferred group of mammals are the bovids which include any milk-producing member of the genus Bos, preferably cows, sheep and goats, most preferably cows.

The antigen-containing shaped matrix material of the present invention can be generally formed from any polymeric material which is biocompatible preferably and biodegradable or bioerodible. The term biocompatible means that the matrix material must be compatible with the tissues of the mammal and more particularly the muscle tissues of the mammal in that it does not result in inflammation of the tissues and must not itself cause an immune reaction. The term biodegradable means that the matrix material of the shaped antigen-containing object must be easily broken down by body processes into smaller molecular units which are readily disposed of or are easily oxidized by the body. The molecular units themselves, just like the macromolecular matrix material, must also be biocompatible. If the matrix material is not biodegradable, it must be at least bioerodible, or otherwise permeable porous to allow release of the encapsulated antigenic substance into the body.

Because the delivery system of the present invention is a solid, shaped mass of matrix material and not a fluid medium, once the shaped matrix material is administered to a mammal, the encapsulated antigenic substance is not immediately released to the body as is the case for antigens in a liquid vehicle, but rather the antigenic substance is slowly released in a controlled fashion over extended periods of time. The rate at Which antigens are released to the system is dependent upon the matrix material employed, its porosity, the rate at which the matrix material degrades or erodes among other factors. Of course, each individual matrix material exhibits its own characteristic rate of release. The rate of antigen release must be fast enough for the body to exhibit an immune response, and not too fast such that most or all of the encapsulated antigen is released within a very short period. The release of antigenic substance from the shaped matrix material may occur by diffusion of the agent from the matrix material or by erosion of the matrix material or by a combination of both factors.

Suitable polymeric matrix materials from which the shaped matrix material containing antigenic subtance can be formed include aliphatic polyesters, polyorthoesters, polyanhydrides, polyamides, polycyclic thioethers, copolyoxalates, polyvinyl alcohol, polypeptides and polydioxanones. Preferred polymeric matrix materials include polylactic acid, polyglycolic acid, poly(lactic acid-co-glycolic acid), polycaprolactone, copolyoxalates, ethylene vinyl/acetate copolymers, and the like. Other suitable polymeric materials include proteins such as collagen and the like, fatty acid esters such as the glycerol stearates and cellulose esters such as cellulose acetate butyrate.

In preparing the antigen containing matrix material of a particular shaped structure, compositions of different rates of controlled release can be prepared. One suitable method of formulation is to incorporate a single antigen or a mixture of at least two antigens into a single matrix material of a particular structure. This process is repeated one or more times with a different matrix material having a different rate of release characteristic from that of the previously employed matrix material. Finally, the antigen containing shaped structures are blended together to prepare an antigen releasing formulation having a range of release rates. Alternatively, an antigen containing shaped structure can be prepared by incorporating a single antigen or mixture of antigens in a blend of two or more different matrix materials to prepare a product in which each shaped structure is made up of a blend of the matrix materials used in the preparation.

The shaped antigen-containing matrix material in a preferred embodiment of the invention is a plurality of microparticles which contain the antigenic substance incorporated throughout the matrix material of the microparticles. The microparticles can be of any shape since shape is not a critical factor associated with release of the entrapped antigenic substance. Generally, however, the microparticles will be spherical in shape. In a preferred method of production spherically shaped microparticles are prepared and the microspheres are between 1 to 500 microns, preferably 10 to 200 microns in diameter. The rate of release of antigen from the microparticles is related to size in some formulations.

In order to place the microparticles in administratable form, the microparticles are placed in an appropriate liquid vehicle for injection into the body such as a saline solution containing a small amount of surfactants.

The molecular weight of the particular matrix material chosen is not a critical factor in the manufacture and use of the shaped, antigen-containing matrix material of the present invention. While an increase in the molecular weight of the polymer may gradually retard the rate of release of antigenic material from the matrix material, these factors may easily be compensated for by determining the rate of release of antigenic substance from the matrix material by in vivo or in vitro measurements and then adjusting the amount of shaped, antigen-containing matrix material administered and the other design parameters such as microparticle size and percent by weight of the antigen in view of the results obtained from the release measurements.

In the manufacture of the microparticles containing antigen, any conventional method of forming the microparticles can be used. The selection of a particular method chiefly depends upon the technical requirements of the matrix material and the particular manner in which the microparticles are intended to be used.

Generally, microencapsulation processes can be classified according to the three principal types of: (1) phase-separation methods including aqueous and organic phase separation processes, melt dispersion and spray drying; (2) interfacial reactions including interfacial polymerization, in situ polymerization and chemical vapor deposition; and (3) physical methods, including fluidized-bed spray coating, multi- and single-orifice centrifugal coating, electrostatic coating and physical vapor deposition.

Phase separation methods, as the term implies, rely on differential solubility characteristics that cause a wall- or shell -forming matrix material to separate from solution or suspension and deposit around particles or droplets of the antigenic substance to be encapsulated. The separation, itself, may be brought about physically, as by the addition of a non-solvent or by a change in temperature, or chemically, as by a change in pH.

An organic phase-separation process usually employs a dispersion or an emulsion of the antigenic substance in a solution or a high-molecular-weight polymer in an organic solvent. To this mixture is added a non-solvent or liquid polymer that causes the high-molecular-weight polymer to separate from solution and collect as a shell around the suspended therapeutic agent(s). The shell, still swollen with solvent, is then hardened by a further addition of non-solvent or by some other process that strengthens the shell and improves the barrier properties.

Typically, an aqueous solution or suspension of a lipophobic antigen is added to a non-aqueous solution of a suitable matrix polymer, and the mixture is agitated to cause the formation of a water-in-oil emulsion. Depending upon its solubility in water, the agent may be present at a concentration of 5 to 50% in the aqueous phase, which may be 5 to 20% by weight of the total mixture. The external organic phase may contain 5 to 10% of the matrix polymer. Usually, however, the ratio of agent in the internal phase (aqueous solution or suspension) to polymer is 2:1 to 1:4. The polymer must be a good film-former; that is, it must possess adequate strength and toughness.

An aqueous phase separation process employs a dispersion or an emulsion of a water-insoluble antigenic substance in an aqueous solution or dispersion of a polymer. The polymer is caused to separate as gel particles; these collect around the therapeutic agent to form a shell; the shell is hardened; and the microparticles are isolated. In the coacervation process, which is the most common of the aqueous phase-separation processes the water-insoluble therapeutic agent, which may be in the form of particles or droplets, is usually dispersed in an aqueous sol of a hydrophilic colloid which becomes ionized in water; a second sol of opposite charge is added; and the mixture is caused to gel by a dilution with water, an addition of salt, an adjustment of pH, or a change in temperature, or any combination of these procedures. Appropriate conditions of coacervation are usually determined experimentally, because the various polymers, possible for use, differ significantly in physical and chemical properties according to source and method of isolation or preparation. A region of coacervation is determined by combining solutions or sols of two polymers at various concentrations, temperatures and levels of pH, and observing the conditions required for gelation. From these determinations can be drawn a ternary phase diagram, showing the area of compatibility and the region of coacervation, at a given temperature and pH. The changes in concentration, temperature or pH to effect gelation will then become apparent.

Each preparation of microparticles requires careful control of conditions, and somewhat different conditions are required for various materials being encapsulated. The degree of agitation, for example, affects the size of emulsion droplets, and the surface properties of the droplets may require alterations in the procedures to insure deposition of matrix material about the droplets and to minimize formation of particles not participating in microencapsulation. The volume of water added in the dilution step is not critical, but generally larger volumes are required to maintain a stable emulsion when larger droplets are encapsualted.

The above phase separation can be adapted to an alternate technique in which the first step of forming a stable emulsion or suspension of a substance is accomplished by dispersing the agent in a solution of the matrix material. Thereafter, the emulsion is added dropwise to a non-solvent with stirring to precipitate the polymer coating material to form microparticles.

Another type of phase separation technique is the melt-dispersion microencapsulation technique. This method can be used with a wide variety of substances to be encapsulated. Usually a heat-liquefiable, waxy coating material, preferably of a low-melting wax such as glycerol distearate is suspended in an inert liquid such as a silicone oil or a fluorocarbon in which neither the wax nor the material to be encapsulated is appreciably soluble. The mixture is heated and stirred vigorously to melt and emulsify the wax. The therapeutic agent which has been powdered and screened to the desired size range, and the waxy coating material are dispersed with high shear agitation, and the liquefied wax coats the therapeutic agent to form the waxy liquid-coated microparticles. Thereafter, the formed microparticles are solidified by continued agitation which cools the particles. The microparticles are then isolated by filtration and dried as described earlier.

The second major method of forming the microparticles is by interfacial microencapsulation which involves bringing two reactants together at a reaction interface where polycondensation of the reactants, usually monomers, occurs to form a thin, insoluble polymeric film. One technique of establishing the interface for the encapsulation process is the dispersion or emulsification of the antigenic substance with one of the reactants which form the condensation polymer in a continuous phase containing the second reactants.

The third major category of encapsulation techniques which is especially applicable to a variety of medicinal or therapeutic agents and coating materials is physical microencapsulation. The physical microencapsulation techniques are characterized by the continuous envelopment of particles or droplets of a substance in a fluid film, as a melt or solution of the coating material, in an apparatus containing coaxially- or sequentially-spaced orifices. Thereafter, the fluid coating is hardened by a standard cooling technique or by solvent evaporation.

Among the physical methods for microencapsulation are those that involve the passage of liquid or solid core material through a liquid matrix material. The stream is disrupted by some means to cause the formation of liquid-coated droplets or particles, and the resulting particles are cooled or otherwise treated to solidify the shell material. For example, an aqueous solution of a substance to be encapsulated is aspirated into rapidly flowing stream of molten glycerol distearate, and the mixture is ejected through a fine nozzle. On emergence from the nozzle, the liquid stream disintegrates into droplets, each consisting of an aqueous core surrounded by liquid wax. As these fall through air, the shells cool and solidify, and microparticles result. In another version of this process, the impelling force is supplied by a rotating member, which ejects the core material centrifugally through the shell-forming liquid.

The variations of these and other processes of microencapsulation are many. As is readily apparent to those skilled in the art, no one process nor any single set of conditions is applicable to all substances, but instead a useful process is chosen and the conditions optimized to achieve the desired results with a specific agent.

In a preferred method of preparing microparticles containing an antigenic substance, a phase separation technique is employed whereby a solution of the polymeric matrix material in a suitable organic solvent is prepared. To this solution is added the antigenic substance suspended or dissolved in water or as fine particles alone. A non-solvent for the polymeric matrix material is slowly added to the stirred dispersion causing the polymeric material to slowly precipitate around the antigenic substance forming microparticles. The microparticles are further hardened by the addition of a second non-solvent for the polymeric matrix material.

The microparticles are then isolated by filtration and dried.

In other embodiments of the invention, the shaped, antigenic substance containing matrix material can assume forms other than microparticles such as rods, wafers, rectangularly shaped films or blocks. In each case the antigenic substance is distributed throughout the matrix material. The amount of antigenic substance dispersed throughout the matrix is an amount sufficient to elicit an immune response as the entrapped antigenic substance is released by the implanted matrix material over an extended period of time. These shaped objects ar particularly suitable for subcutaneous implantation into a mammal desired to be immunized.

Yolles, in U.S. Pat. No. 3,887,699, discloses drug-containing shaped polymeric objects of assorted shapes and sizes for subcutaneous implantation in a subject. This patent is incorporated by reference into the present specification insofar as it shows the preparation of various shaped objects from biocompatible and biodegradable polymeric matrix materials which objects are quite suitable for subcutaneous implantation and insofar as it shows method of preparing biocompatible and biodegradable polymeric material of assorted shapes.

The shaped, antigenic substance containing matrix material can be administered in several ways. When the shaped matrix is in the form of microparticles, the most expedient mode of administration is by intramuscular injection, although microparticles can be subcutaneously implanted. For matrix material which is shaped into such objects as rods, wafers, films and the like, the most common and expedient mode of administration is by subcutaneous implantation.

The desired objective of the present invention is to bring a mammal into a hyperimmune state, as well as to produce antibodies and lymphokinen factors in milk. By conventional administration procedures this state is usually achieved by an initial inoculation of a mammal with an antigen or mixture of antigens in a liquid vehicle, followed by several booster injections of sufficiently high doses of antigen or mixtures of antigens which are necessary to reach a hyperimmune state. Normally, booster injections are used at two-week intervals to reach and maintain high antibody titer levels in the body fluids of a mammal. It is only when the mammal is in a hyperimmune state that the body fluids of the mammal will contain a sufficiently high antibody titer. In the case of a bovid such as a cow, the milk of a hyperimmunized cow will have a high level of immune regulatory factor which makes the milk useful for a variety of different purposes.

The advantage of the present invention is that by a single implantation of a shaped, antigenic substance containing matrix material, not only are booster injections of the antigenic substance not needed to reach a hyperimmune state, but quite unexpectedly and even more importantly, higher levels of immune regulatory factors including antibodies and lymphokinens within the mammal and in the milk of cows can be obtained in comparison to conventional inoculation methods. Because in the present technique the antigenic substance is dispersed throughout the matrix material, it is gradually released from the matrix material thereby providing a sustained, continual release of antigenic substance to the treated mammal. This mode of administration of antigenic substance is quite different from inoculations of antigenic substance where a given quantity of antigenic substance is administered instantaneously followed by depletion of the level of antigenic substance in the body of the mammal until the next inoculation with antigenic substance. For this reason it is very difficult to state just how much antigenic substance is administered to a mammal being immunized by the method of the present invention. Perhaps a given mammal may be administered antigenic substance at a rate of 0.01 to 1.0 mg per day. It may be that the unexpectedly high immune regulatory factor levels achieved by the method of the present invention are attributable to the fact that antigenic substance levels are maintained at relatively constant levels for extended periods of time within the body tissues of the mammal being treated. It is apparent that whatever specific mode the shaped, antigenic substance containing matrix material of the present invention is administered, the delivery system must contain enough antigenic substance to maintain a continued level of antigenic substance for a time sufficient to reach a hyperimmune state. For example, approximately $10^9$ killed bacterial cells can be used in a normal dose per injection, but this number certainly can vary with the type of antigen used.

In another embodiment of the present invention, even higher antibody titers can be obtained by a modification of the present implantation method wherein simultaneously with the implantation of a shaped, antigenic subtance containing matrix material, the subject mammal is administered unencapsulated antigenic substance. In other words, the subject mammal at the time of implantation can be inoculated in some manner with unencapsulated antigenic substance, there placing the subject mammal in the state of an immediate high antigen level. This procedure results in the desirable effect of providing higher antibody titers in the subject animal more rapidly than the rate at which high titer levels can be reached only by the basic implantation technique. In the embodiment of the invention where microparticles are being subcutaneously or intramuscularly injected, antigenic substance in a liquid vehicle can be inoculated right along with the microparticles or at another site on the subject mammal. When the shaped matrix material is implanted in a subject animal, unencapsulated antigenic substance may be implanted with the shaped, antigenic substance containing matrix material or it can be inoculated into the subject animal at a different site.

It is necessary to determine whether or not the inoculated mammal has become sensitive to the antigenic substance. There are a number of methods known to those skilled in the art of immunology to test for sensitivity, (*Methods in Immunology and Immuno-Chemistry*, William, C. A., Chase, W. M., Academic Press, N.Y., London, Vol. 1-5, 1977). Examples of these tests include skin sensitivity tests, serum tests for the presence of antibodies to the stimulating antigens and tests designed to evaluate the ability of immune cells from the host to respond to the antigen. The type of test employed will depend to a large extent on the nature of the antigenic substance used. The preferred method is to use a polyvalent vaccine consisting of multiple bacterial species as the antigenic substance and to test for the presence of agglutinating antibodies in the serum of the mammal before and after challenge with the vaccine. In the case of a bovid, the appearance of milk antibodies after immunization with the vaccine is indicative of sensitivity, and at this point the antibody-containing milk produced by the bovid can be utilized for the purpose desired.

Any specific antigen or combination of antigens may be employed as the antigenic substance for incorporation in the shaped matrix material and subsequent implantation in the subject mammal. The antigens can be bacterial, viral, cellular or any other substance to which the immune system of the mammal will respond. Preferably, the antigen or mixtures of antigens are bacterial or viral with polyvalent antigens also being preferred. Suitable bacterial antigens include Neisseria gonorrhea, Mycobacterium tuberculosis, Haemophilus vaginalis, Group b Streptococcus ecoli, Microplasma hominis, Staphylococcus aureus, Staphylococcus epidermidis, Streptococcus pyrogenes, Streptococcus mutans, Aerobacter aerogenes, Escherichia coli, Salmonella enteritidis, Pseudomonas aeruginosa, Klebsiella pneumoniae, Salmonella typhimurium, Haemophilus influenzae, Streptococcus viridans, Proteus vulgaris, Shigella dysenteriae, Streptococcus Group B, Diplococcus pneumoniae, Corynebacterium Acne Types 1 and 2, Hemophilus ducreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis, Chlamydia psittaci, Escherichia coli, Actinobacillus equuli, Salmonella abortus ovis, Salmonella abortus equi, Corynebacterium equi, Corynebacterium pyogenes, Actinobaccilus seminis, Mycoplasma bovigenitalium, Clostridium tetani, Pseudomonas maltophiia, Streptococcus equisimili, Streptococcus dysgalactiae, Streptococcus uberis, Streptococcus bovis, Pasteurella multocida, Pasteurella hamemolytica, Moraxella bovis, Actinobacillus lignieresi, Corynebacterium renale, Fusobacterium necrophorum, Bacillus cereus, Salmonella dublin, Salmonella heidleberg, Salmonella paratyphi, and Yersinia enterocolitica. Suitable viral antigens include Equine herpes virus, Equine arteritis virus, IBR—IBP virus, BVD—MD virus and Herpes virus (humonis types 1 and 2).

The method of the present invention can be used to produce a high level of immunity in a mammal. Accordingly, milk-producing bovid animals can be hyperimmunized by the present technique to produce the antibody and lymphokinen containing milk. The lymphokinen factors are effective against inflammations, as described in U.S. Pat. No. 4,284,623, and other conditions which are debilitating cardiovascular and pulmonary conditions as described in application Ser. No. 546,162 filed Oct. 27, 1983 now U.S. Pat. No. 4,636,384. The method of the present invention can also be used to produce the specific antibody-containing milk which is effective against the bacteria which promote dental caries formation, plaque formation and gingivitis as described in U.S. Pat. No. 4,324,782 or to produce the antibody-containing milk which is effective against odor and disease causing skin bacteria as described in copending applications Ser. Nos. 370,139 and 399,266, filed Apr. 20, 1982 now abandoned and July 18, 1982 now abandoned, respectively. Alternatively, the method of the present invention can be used as a general technique of immunizing all mammals against diseases which a given mammal can be immunized against; said mammals including human beings.

Having generally described this invention, a further understanding can be obtained by reference to certain specific examples which are provided herein for purposes of illustration only and are not intended to be limiting unless otherwise specified.

PREPARATION OF S-100 VACCINE

A bacterial culture containing the spectrum of bacteria shown in Table 1 below as obtained from the American Type Culture Collection was reconstituted with 15 ml of media and incubated overnight at 37° C. Once good growth was obtained, approximately one-half of the bacterial suspension was employed to inoculate one liter of broth with the inoculate being incubated at 37° C. The remaining suspension was transferred to sterile glycol tubes and stored at −20° C. for up to six months.

After good growth was visible in the liter culture, the bacterial cells were harvested by centrifugation of the suspension for twenty minutes to remove the media. The bacterial pellet obtained was resuspended in sterile saline solution and the bacterial sample was centrifuged three times to wash the media from the cells. After the third sterile saline wash, bacterial pellet obtained upon centrifugation was resuspended in a small amount of double distilled water.

The media-free bacterial suspension was heat-killed by placing the suspension in a glass flask in an 80° C. water bath overnight. The viability of the bacteria in the sample was determined by inoculation of the broth culture with a small amount of the heat-killed bacteria. The broth was incubated at 37° C. for five days and checked daily for growth, since the bacteria have to be killed for use in the vaccine.

The heat killed bacteria were lyophilized until dry. The dry bacteria were then mixed with sterile saline solution to a concentration of $2.2 \times 10^8$ bacterial cells/ml saline (1.0 optical density reading at 660 nm).

TABLE 1

| S-100 Bacteria List | | | |
|---|---|---|---|
| Name | Media | Gram + or − | ATCC # |
| 1. Staph. aureus | BHI | + | 11631 |
| 2. Staph. epidermidis | BHI | + | 155 |
| 3. Strep. pyogenes, A. Type 1 | APT | + | 8671 |
| 4. Strep. pyogenes, A. Type 3 | APT | + | 10389 |
| 5. Strep. pyogenes, A. Type 5 | APT | + | 12347 |
| 6. Strep. pyogenes, A. Type 8 | APT | + | 12349 |
| 7. Strep. pyogenes, A. Type 12 | APT | + | 11434 |
| 8. Strep. pyogenes, A. Type 14 | APT | + | 12972 |
| 9. Strep. pyogenes, A. Type 18 | APT | + | 12357 |
| 10. Strep. pyogenes, A. Type 22 | APT | + | 10403 |
| 11. Aerobacter aerogenes | BHI | − | 884 |
| 12. Escherichia coli | BHI | − | 26 |
| 13. Salmonella enteritidis | BHI | − | 13076 |
| 14. Pseudomonas aeruginosa | BHI | − | 7700 |
| 15. Klebsiella pneumoniae | BHI | − | 9590 |
| 16. Salmonella typhimurium | BHI | − | 13311 |
| 17. Haemophilus influenzae | BHI | − | 9333 |
| 18. Strep. mitis | APT | + | 6249 |
| 19. Proteus vulgaris | BHI | − | 13315 |
| 20. Shigella dysenteriae | BHI | − | 11835 |
| 21. Diplococcus pneumoniae | APT | + | 6303 |
| 22. Propionibacter acnes Actinomyces (anaerobe) | Broth | + | 11827 |
| 23. Strep. sanguis | APT | + | 10556 |
| 24. Strep. salivarius | APT | + | 13419 |
| 25. Strep. mutans | BHI | + | 25175 |
| 26. Strep. agalactiae | APT | + | 13813 |

EXAMPLE 1

Eight cows identified by number in Table 2 below were given daily injections of 5 ml samples of the polyvalent liquid vaccine. Antibody (IgG) titer levels for the injected cattle were determined periodically. The antibody (IgG) titer levels were determined by using an enzyme linked immuno-assay (ELISA) system, the end point being an optical density reading at 410 nm of antibody containing fluid samples obtained from cow's milk, the individual reading obtained from each cow being shown in Table 2 below. The higher the optical density reading, the higher the titer. The table also shows the average optical density reading determined from the individual optical density values obtained. The average IgG antibody titer level as determined from the average optical density value for each measurement period is also shown in Table 2. The FIGURE is a graph of the results shown in Table 2.

bers 398, 408, 414 and 400 in Table 3 below were treated by an injection of microparticle containing solution prepared as described above.

The four cows were injected intramuscularly with the polyvalent antigen containing microparticles on Apr. 23, 1982. Microparticle samples B022-41-1 and BO22-41-2 were sterilized with 2.0 mRad of gamma radiation, while samples BO22-41-3 and BO22-41-4 were unsterilized. Antibody (IgG) titer levels were determined periodically from samples of cow's milk obtained from the inoculated cows as well as the control cows, and the data obtained are shown in Table 3.

TABLE 2

| Cow No. | 2/9/83 | 2/15/83 | 2/20/83 | 2/25/83 | 3/2/83 | 3/7/83 | 3/12/83 | 3/17/83 | 3/21/83 | 3/24/83 | 5/18/83 |
|---|---|---|---|---|---|---|---|---|---|---|---|
| 2245 | 0.352 | 0.329 | 0.391 | 0.544 | 0.646 | 0.512 | 0.421 | 0.383 | 0.333 | 0.328 | — |
| 2033 | 0.410 | 0.304 | 0.345 | 0.614 | 0.522 | 0.399 | 0.360 | 0.409 | 0.307 | 0.306 | 0.332 |
| 1805 | 0.386 | 0.466 | 0.560 | 1.009 | 0.640 | 0.510 | 0.354 | 0.304 | 0.257 | 0.380 | — |
| 2195 | 0.365 | 0.279 | 0.405 | 0.504 | 0.493 | 0.433 | 0.348 | 0.265 | 0.227 | 0.232 | 0.295 |
| 1761 | 0.448 | 0.251 | 0.348 | 0.577 | 0.404 | 0.324 | 0.481 | 0.391 | 0.273 | 0.332 | — |
| 2345 | — | — | — | — | — | — | — | — | — | — | 0.338 |
| 2093 | — | — | — | — | — | — | — | — | — | — | 0.429 |
| 2429 | — | — | — | — | — | — | — | — | — | — | 0.235 |
| AVG. | 0.392 | 0.326 | 0.410 | 0.650 | 0.541 | 0.436 | 0.393 | 0.350 | 0.279 | 0.316 | 0.326 |
| IgG Conc. (mg/ml) | 0.557 | 0.629 | 0.701 | — | 0.657 | 0.501 | — | 0.468 | — | 0.379 | 0.529 |

| Cow No. | 5/20/83 | 5/25/83 | 5/31/83 | 6/6/83 | 6/10/83 | 6/15/83 | 6/20/83 | 6/24/83 | 6/29/83 | 7/5/83 | 7/11/83 |
|---|---|---|---|---|---|---|---|---|---|---|---|
| 2245 | — | — | — | — | — | — | — | — | — | — | — |
| 2033 | 0.426 | 0.598 | 0.673 | 0.731 | 0.756 | 0.467 | 0.585 | — | — | — | — |
| 1805 | — | — | — | — | — | — | — | — | — | — | — |
| 2195 | 0.299 | 0.466 | 0.631 | 0.589 | 0.638 | 0.612 | 0.619 | 0.637 | 0.731 | 0.727 | 0.759 |
| 1761 | — | — | — | — | — | — | — | — | — | — | — |
| 2345 | 0.333 | 0.445 | 0.750 | 0.508 | 0.643 | 0.635 | 0.592 | 0.562 | 0.591 | 0.532 | 0.475 |
| 2093 | 0.441 | 0.531 | 0.618 | — | — | — | — | — | — | — | — |
| 2429 | 0.276 | 0.286 | 0.356 | 0.466 | 0.478 | 0.539 | 0.449 | 0.464 | 0.503 | 0.554 | 0.662 |
| Average | 0.355 | 0.465 | 0.606 | 0.574 | 0.629 | 0.563 | 0.561 | 0.554 | 0.608 | 0.604 | 0.632 |
| IgG Conc. (mg/ml) | 0.640 | 0.612 | 0.543 | — | — | — | — | — | — | — | — |

| Cow No. | 7/15/83 | 7/21/83 | 7/27/83 | 8/2/83 | 8/8/83 | 8/12/83 | 8/15/83 | 8/17/83 | 8/22/83 |
|---|---|---|---|---|---|---|---|---|---|
| 2245 | — | — | — | — | — | — | — | — | — |
| 2033 | — | — | — | — | — | — | — | — | — |
| 1805 | — | — | — | — | — | — | — | — | — |
| 2195 | 0.581 | 0.654 | 0.550 | 0.636 | 0.613 | 0.663 | 0.740 | 0.671 | 0.712 |
| 1761 | — | — | — | — | — | — | — | — | — |
| 2345 | 0.578 | 0.643 | 0.611 | 0.581 | 0.584 | 0.597 | 0.592 | 0.589 | 0.692 |
| 2093 | — | — | — | — | — | — | — | — | — |
| 2429 | 0.637 | 0.688 | 0.877 | 0.489 | 0.498 | 0.425 | 0.518 | 0.504 | 0.474 |
| Average | 0.599 | 0.662 | 0.679 | 0.569 | 0.565 | 0.562 | 0.617 | 0.588 | 0.626 |
| IgG Conc. (mg/ml) | — | — | — | — | — | — | — | — | — |

Remarks:
Optical density readings at 410 nm.
Injections given daily 2/9/82-2/22/83 and 5/18/83 to 10/12/83.

EXAMPLE 2

Heat-killed bacteria were prepared in the manner described above. The polyvalent antigen sample (S-100) obtained was microencapsulated by a conventional phase-separation process to prepare a polyvalent antigen containing microparticle product. The polymeric matrix material employed was biodegradable poly (lactide -co-glycolide). The microparticles were less than 250 microns in diameter. Approximately 750 mg of microparticles containing 22% (16.5 mg) of polyvalent antigen was then suspended in about 3 cc. of a vehicle (1 wt % Tween 20 and 2 wt % carboxymethyl cellulose in water).

A small group of cattle was selected from a larger herd of cattle. Five of these randomly selected cattle were selected as controls. Four cattle identified as num-

TABLE 3

Electroimmunoassay & Microtiter Results of Serum Samples from Microencapsulated vs. Random S-100 Cows. Date 7-13-82

Experimental Design:

| Cow | Antigen | Vehicle |
|---|---|---|
| 408 | B022-41-1 | B022-042-1 |
| 400 | B022-41-2 | B022-42-2 |
| 398 | B022-41-3 | B022-42-3 |
| 414 | B022-41-4 | B022-42-4 |

| | Cow No. Date of Sample | Cows Treated with Microencapsulated Antigen 2 | | | | | Control Cows 1 |
|---|---|---|---|---|---|---|---|
| | | 398 | 408 | 414 | 400 | Mean | Mean |
| | 4-29-82 | 18.9 | 24.2 | 29.1 | 28.2 | 25.1 | 26.6 |
| | 5-13-82 | 19.2 | 22.0 | 46.5 | 36.6 | 31.1 | 28.7 |
| $I_gG$ | 6-2-82 | 26.7 | 25.7 | 41.2 | 39.4 | 33.3 | 32.8 |
| Level | 6-16-82 | 31.0 | 27.0 | 39.7 | 39.4 | 34.2 | 33.5 |

TABLE 3-continued

Electroimmunoassay & Microtiter Results of Serum Samples from Microencapsulated vs. Random S-100 Cows. Date 7-13-82

Experimental Design:

| | Cow | Antigen | Vehicle |
|---|---|---|---|
| | 408 | B022-41-1 | B022-042-1 |
| | 400 | B022-41-2 | B022-42-2 |
| | 398 | B022-41-3 | B022-42-3 |
| | 414 | B022-41-4 | B022-42-4 |

| | | Cows Treated with Microencapsulated Antigen 2 | | | | Control Cows 1 |
|---|---|---|---|---|---|---|
| Cow No. Date of Sample | 398 | 408 | 414 | 400 | Mean | Mean |
| (mg/ml) 6-30-82 | 27.6 | 32.9 | 39.1 | 31.3 | 32.7 | 31.2 |
| Mean | 24.7 | 28.0 | 39.1 | 34.9 | 31.3 | 30.6 |
| 4-28-82 | 376 | 128 | 768 | 512 | 376 | 576 |
| Micro- 5-13-82 | 608 | 768 | 384 | 768 | 608 | 512 |
| liter 6-2-82 | 608 | 256 | 384 | 768 | 608 | 640 |
| 6-16-82 | 1536 | 1536 | 1536 | 1024 | 1536 | 704 |
| 6-30-82 | 1472 | 1024 | 2048 | 2048 | 1472 | 536 |
| Mean | 890 | 742 | 1024 | 1024 | 920 | 594 |

Note:
1. Five control cows were randomly chosen from the S-100 herd.
2. Microencapsulated cows:
398 calved on 5-28-82
408 calved on 5-27-82
414 calved on 5-15-82
400 calved on 5-20-82

The results obtained from Examples 1 and 2 show that the technique of the present invention for achieving an immune state in an animal, particularly a bovid animal, by fewer inoculations with antigen containing microparticles is superior to conventional methodology of achieving an immune state in an animal by inoculation with conventional antigen containing injectable solutions.

Having now fully described the invention, it will be apparent to one of ordinary skill in the art that many changes and modifications can be made thereto without departing from the spirit or scope of the invention as set forth herein.

What is claimed as new and is intended to be secured by Letters Patent is:

1. A method for providing milk having an elevated IgG antibody level comprising implanting intramuscularly or subcutaneously within a bovid mammal an antigenic substance in an amount effective to elicit a hyperimmunization response, said antigenic substance being incorporated within shaped microparticles of a biocompatible matrix material which causes controlled release of said antigen, thereby prolonging antigenic activity within said bovid mammal, and recovering milk having an elevated, higher than normal level of IgG antibody.

2. The method of claim 1, wherein the matrix material of said microparticles is a biocompatible, biodegradable polymeric matrix material.

3. The method of claim 2, wherein said polymeric material is polylactic acid, polyglycolic acid, poly(lactic acid-co-glycolic acid), polycaprolactone, polyoxalic acid, polydioxanone, polyorthoester or the salt form of these polymers.

4. The method of claim 1, wherein said antigenic substance, is a plurality of at least two antigens.

5. The method of claims 1 or 4, wherein an antigen or said plurality of at least two antigens in said shaped structure is prepared by incorporating said antigen or at least two antigens in a mixture of at least two different biodegradable, biocompatible polymers, each having a different rate of biodegradation, thereby forming individual microparticles composed of a mixture of polymeric matrix materials.

6. The method of claim 1 or 4, wherein an antigen or said plurality of at least two antigens in said shaped structure is prepared by (a) incorporating said antigen or said at least two antigens in a single polymeric matrix material, (b) separately repeating the process of step (a) at least once with a different polymeric matrix material having a rate of biodegradation different from the first used matrix material of step (a), and then (c) completing the preparation of the microparticle formation by blending the separately prepared antigen containing microparticle batches.

7. The method of claim 5, wherein said at least two different biodegradable, biocompatible polymers are selected from the group consisting of polylactic acid, polyglycolic acid, poly(lactic acid-co-glycolic acid), polycaprolactone, polyoxalic acid, polydioxanone, polyorthoester and the salt form of these polymers.

8. The method of claim 6, wherein the polymeric materials employed in said separate microparticle preparation steps are selected from the group consisting of polylactic acid, polyglycolic acid, poly(lactic acid-co-glycolic acid), polycaprolactone, polyoxalic acid, polydioxanone, polyorthoester and the salt form of these polymers.

9. The method of claim 1, wherein said antigenic substance is a single bacterial antigen or a mixture of at least two bacterial antigens.

10. The method of claim 9, wherein said antigenic substance is at least a single bacterial antigen selected from the group consisting of *Neisseria gonorrhea, Mycobacterium tuberculosis, Haemophilus vaginalis,* Group b *Streptococcus ecoli, Microplasma hominis, Staphylococcus aureus, Staphylococcus epidermidis, Streptococcus pyrogenes, Streptococcus mutans, Aerobacter aerogenes, Escherichia coli, Salmonella enteritidis, Pseudomonas aeruginosa, Klebsiella pneumoniae, Salmonella typhimurium, Haemophilus influenzae, Streptococcus viridans, Proteus vulgaris, Shigella dysenteriae, Streptococcus Group B, Diplococcus pneumoniae, Corynebacterium Acne* Types 1 and 2, *Hemophilus ducreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis, Chlamydia psittaci, Escherichia coli, Actinobacillus equuli, Salmonella abortus ovis, Salmonella abortus equi, Corynebacterium equi, Corynebacterium pyogenes, Actinobaccilus seminis, Mycoplasma bovigenitalium, Clostridium tetani, Pseudomonas maltophiia, Streptococcus equisimili, Streptococcus dysgalactiae, Streptococcus uberis, Streptococcus bovis, Pasteurella multocida, Pasteurella haemolytica, Moraxella bovis, Actinobacillus lignieresi, Corynebacterium renale, Fusobacterium necrophorum, Bacillus cereus, Salmonella dublin, Salmonella heidleberg, Salmonella paratyphi,* and *Yersinia enterocolitica.*

11. The method of claim 1, wherein said bovid is a cow.

12. The method of claim 1, wherein said antigenic substance containing shaped matrix material is in the form of microspheres, rods, wafers or films.

13. The method of claim 1, wherein said antigenic substance is an antigen or mixture of antigens of bacterial, viral or cellular origin.

14. The method of claim 1, wherein said immunized state is attained by simultaneously implanting said antigenic substance containing shaped matrix material in said mammal and inoculating said mammal with a fluid containing said antigenic substance.

* * * * *